United States Patent [19]
Kitada et al.

[11] Patent Number: 5,801,147
[45] Date of Patent: Sep. 1, 1998

[54] POLYPEPTIDES AND USE THEREOF

[75] Inventors: Chieko Kitada, Osaka; Takuya Watanabe, Ibaraki, both of Japan

[73] Assignee: Takeda Chemical Industries, Ltd., Osaka, Japan

[21] Appl. No.: 766,725

[22] Filed: Dec. 13, 1996

Related U.S. Application Data

[63] Continuation of Ser. No. 932,455, Aug. 18, 1992, Pat. No. 5,623,050.

[30] Foreign Application Priority Data

Aug. 22, 1991 [JP] Japan .................... 3-211161

[51] Int. Cl.$^6$ ............ A61K 38/00; C07K 14/00
[52] U.S. Cl. .............. 514/12; 530/324; 530/326
[58] Field of Search .................. 530/324; 514/12

[56] References Cited

U.S. PATENT DOCUMENTS

| | | | |
|---|---|---|---|
| 4,562,175 | 12/1985 | Chang et al. | 514/12 |
| 4,605,641 | 8/1986 | Bolin et al. | 514/12 |
| 4,757,133 | 7/1988 | Ito et al. | 530/324 |
| 5,128,242 | 7/1992 | Arimura et al. | 435/7.21 |
| 5,208,320 | 5/1993 | Kitada et al. | 530/324 |

FOREIGN PATENT DOCUMENTS

| | | |
|---|---|---|
| 0 241 926 | 10/1987 | European Pat. Off. . |
| 0404652 | 12/1990 | European Pat. Off. . |
| A1-0404652 | 12/1990 | European Pat. Off. . |
| A2-0404034 | 12/1990 | European Pat. Off. . |

OTHER PUBLICATIONS

Watanabe et al, Biochemical and Biophysical Research Communication, pp. 252, 258, vol. 173 No. 1 1990.
Miyata et al, Biochemical and Biophysical Research Communication, vol. 170, No. 2, 1990 pp. 643–648.
Raizada et al, Am. J. Physiol., 247: C364 (1984).
The Endocrine Society 72nd Annual Meeting, p. 340, No. 1261, Jun. 20–23 (1990).
Wantanabe et al., *Biochemical and Biophyscial Research Communications*, 182(1):403–411, 1990.
Watanabe et al., *Biochemical and Biophysical Research Communications*, 173(1):252–258 (1990).
Miyata et al., *Biochemical and Biophysical Research Communications*, 170(2):643–648 (1990).
Protein Engineering; 25:279–287 (1987).
Miyata et al., *Biochemical and Biophysical Research Communications*, 164(1):567–574 (1989).
Kornreich et al., *J. Med. Chem.*, 35:1870–1876 (1992).
Rubberecht et al., *Regulatory Peptide*, 21:117–128 (1988).
Raizada et al., *Am. J. Physiol.*, 247:C364 (1984).
Clarke et al., *J. Biol. Chem.*, 259:11672 (1984).

*Primary Examiner*—Cecilia J. Tsang
*Assistant Examiner*—S. G. Marshall
*Attorney, Agent, or Firm*—David G. Conlin; Peter F. Corless; Dike, Bronstein, Roberts & Cushman, LLP

[57] ABSTRACT

Disclosed are (1) a polypeptide represented by formula (I), or a pharmaceutically acceptable amide, ester or salt thereof:

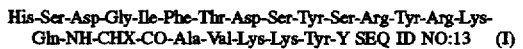

wherein X is hydrogen atom; or a lower alkyl group which may be substituted with a member selected from the group consisting of hydroxy group, substituted or unsubstituted amino group, carboxyl group, carbamoyl group, and substituted or unsubstituted aromatic group; and Y is one of amino acids or peptides consisting of 1 to 16 amino acid residues counted from the N-terminal side of Leu-Ala-Ala-Val-Leu-Gly-Lys-Arg-Tyr-Lys-Gln-Arg-Val-Lys-Asn-Lys SEQ ID NO:20, and (2) a pharmaceutical composition comprising a polypeptide represented by formula (I), or a pharmaceutically acceptable amide, ester or salt thereof, which has remarkable c-AMP activity and is useful as a nerve activating agent.

1 Claim, 1 Drawing Sheet

5,801,147

1
POLYPEPTIDES AND USE THEREOF

This is a continuation of application Ser. No. 07/932,455 filed on Aug. 18, 1992, now U.S. Pat. No. 5,623,050.

BACKGROUND OF THE INVENTION

The present invention relates to novel polypeptides having c-AMP-producing activity, and amides, esters or salts thereof. The present invention further relates to the use thereof.

As a new biologically active peptide derived from the brain hypothalami, the testes or the like, polypeptide PACAP38 consisting of 38 amino acid residues has recently been discovered in humans, sheep and rats. The human-derived, sheep-derived and rat-derived PACAP38 polypeptides which are identical to one another in their amino acid sequence have the following formula:

His-Ser-Asp-Gly-Ile-Phe-Thr-Asp-Ser-Tyr-Ser-Arg-Tyr-Arg-Lys-
Gln-Met-Ala-Val-Lys-Lys-Tyr-Leu-Ala-Ala-Val-Leu-Gly-Lys-Lys-
Arg-Tyr-Lys-Gln-Arg-Val-Lys-Asn-Lys (SEQ ID NO:1).

PACAP38 enhances the production of intracellular c-AMP in hypophysis cells and the production of c-AMP of astroglia cells, which, in turn, increases the survival time of nerve cells. The activity of PACAP38 has also been found in PACAP27-a polypeptide consisting of 27 amino acid residues on the N-terminal side of PACAP38 [*Biochem. Biophys. Commun.*, 164, 567–574 (1989); European Patent Unexamined Publication No. 404,652]. Further, the same activity as that of PACAP27 has also been confirmed in polypeptides PACAP26, PACAP25, PACAP24 and PACAP23 consisting of 26 to 23 amino acid residues, respectively, on the N-terminal side of PACAP38.

The amino acid situated at the 17-position of PACAP38, i.e., methionine, is liable to be oxidized.

SUMMARY OF THE INVENTION

It is therefore an object of the present invention to provide novel polypeptides that are more stable against oxidation and have activity equivalent to or higher than that of PACAP27.

The present inventors produced novel polypeptides that are more stable against oxidation and have c-AMP-producing activity equivalent to or higher than that of PACAP27, and further studied them, thus completing the present invention.

Namely, the present invention provides (1) a polypeptide represented by formula (I), or an amide, an ester or a salt thereof:

His-Ser-Asp-Gly-Ile-Phe-Thr-Asp-Ser-Tyr-Ser-Arg-Tyr-Arg-Lys-
Gln-NH-CHX-CO-Ala-Val-Lys-Lys-Tyr-Y (SEQ ID NO:13) (I)

wherein X represents an hydrogen atom, a hydroxyl group, an amino acid group which may be substituted, a carboxyl group, a carbamoyl group or a lower alkyl group which may be substituted with a substituted or unsubstituted aromatic group; and Y represents one of amino acids or peptides consisting of 1 to 16 amino acid residues counted from the N-terminal side of Leu-Ala-Ala-Val-Leu-Gly-Lys-Arg-Tyr-Lys-Gln-Arg-Val-Lys-Asn-Lys (SEQ ID NO:20); and (2) a pharmaceutical composition comprising a polypeptide represented by formula (I), or an amide, an ester or a pharmaceutically acceptable salt thereof.

Figure 1:
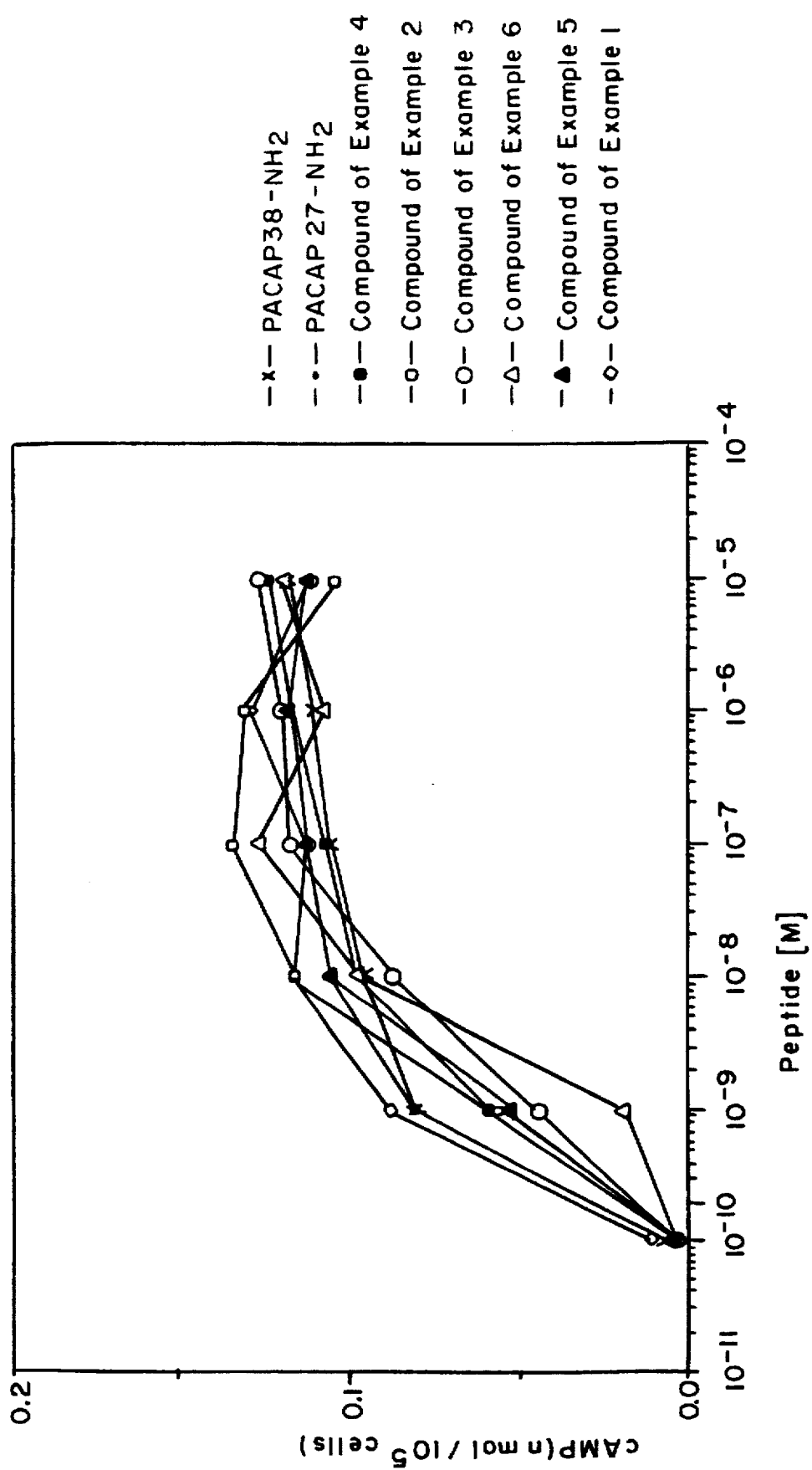
FIG. 1 is a graph comparatively showing c-AMP-producing activity of [Ia-f] which is a compound of the present invention, PACAP27-NH$_2$ and PACAP38-NH$_2$.

2
DESCRIPTION OF THE PREFERRED EMBODIMENTS

For peptides described in this specification, the left ends are the N-termini (amino termini) and the right end is the C-termini (carboxyl termini) according to the convention of the peptide indication.

In formula (I), X is hydrogen atom; or a lower alkyl group which may be substituted with a member selected from the group consisting of hydroxy group, substituted or unsubstituted amino group, carboxyl group, carbamoyl group, and substituted or unsubstituted aromatic group.

As the lower alkyl groups, preferred are straight or branched chain $C_{1-6}$ alkyl groups, which include, for example, methyl, ethyl, n-propyl, isopropyl, n-butyl, isobutyl, sec-butyl, t-butyl, n-pentyl, isoamyl, t-amyl, n-hexyl and isoheptyl. These lower alkyl groups may be substituted by 1 to 3 substituents selected from the group consisting of hydroxyl groups, amino groups which may be substituted, carboxyl groups, carbamoyl groups or aromatic groups which may be substituted. As the lower alkyl groups substituted with hydroxyl groups, preferred are ones in which the above-mentioned $C_{1-6}$ alkyl groups are substituted with hydroxyl groups, which include, for example, hydroxymethyl, 1-hydroxyethyl, 2-hydroxyethyl and 1-hydroxypropyl. As the lower alkyl groups substituted with substituted or unsubstituted amino groups, are preferred ones in which the above-mentioned $C_{1-6}$ alkyl groups are substituted with amino groups (—NH$_2$) or substituted amino groups (for example, mono $C_{1-3}$ alkylamino groups such as methylamino and ethylamino, di $C_{1-3}$ alkylamino groups such as dimethylamino and diethylamino, and guanidino groups), which include, for example, 2-aminoethyl, 2-(methylamino)ethyl, 3-aminopropyl, 4-aminobutyl and 3-guanidinopropyl. As the lower alkyl groups substituted with carboxyl groups, are preferred ones in which the above-mentioned $C_{1-6}$ alkyl groups are substituted with carboxyl groups (—COOH), which include carboxymethyl, 1-carboxyethyl and 2-carboxyethyl. As the lower alkyl groups which may be substituted with carbamoyl groups, are preferred ones in which the above-mentioned $C_{1-6}$ alkyl groups are substituted with carbamoyl groups (—CONH$_2$), which include, for example, carbamoylmethyl, 1-carbamoylethyl and 2-carbamoylethyl. As the lower alkyl groups substituted with substituted or unsubstituted aromatic groups, are preferred ones in which the above-mentioned $C_{1-6}$ alkyl groups are substituted with aromatic groups (for example, $C_{6-12}$ aryl groups such as phenyl and naphthyl, and aromatic heterocyclic groups, especially 5 to 9 membered aromatic heterocyclic groups which contain carbon atoms and 1 to 3 hetero atoms selected from the group consisting of N, O and S, such as imidazolyl, pyrazolyl, indolyl, dihydroindolyl, quinolyl, tetrahrdroquinolyl, isoquinolyl, tetrahydro-isoquinolyl, benzazepinyl, tetrahydrobenzazepinyl, pyrrolyl, piperidyl, piperazinyl, morpholinyl, furanyl, thiophenyl) or substituted aromatic groups (for example, the above mentioned $C_{6-12}$ aryl or 5 to 9 membered aromatic heterocyclic groups which are substituted by 1 to 3 substituents selected from the group consisting of a $C_{1-6}$ alkyl group (ex. methyl, ethyl), halogen atom (ex. chloro, bromo), hydroxy group, carboxyl group, amino group, mono- or di-$C_{1-6}$ alkyl amino group (ex. methylamino, ethylamino, dimethylamino, diethylamino), $C_{1-6}$alkoxy-carbonyl group (ex. formyl, methoxycarbonyl), $C_{1-6}$alkoxy group (methoxy, ethoxy), cyano group and so on, such as 4-hydroxyphenyl, 4-methylphenyl, N-methylindolyl and fluoroindolyl), which include, for example, benzyl, 1-phenylethyl, 2-phenylethyl, 1-naphthylmethyl, 2-naphthylmethyl, 4-hydroxyphenylmethyl, 1H-imidazole-4-ylmethyl, 1H-indole-3-ylmethyl, N-methylindole-3-ylmethyl and 5-fluoro-1H-indole-3-ylmethyl.

In formula (I), X is as mentioned above. In other words, this means that —NH—CHX—CO— is a glycine residue or an a-amino acid residue. As such α-amino acids, natural amino acids including glycine are preferred, which include, for example, alanine, valine, leucine, isoleucine, serine, threonine, lysine, arginine, aspartic acid, asparagine, glutamic acid, glutamine, phenylalanine, tyrosine, histidine and tryptophan. Serine and arginine are particularly preferred among others. These amino acids may be any of the L-, D- and DL-forms, but the L-form is particularly preferred.

In formula (I), Y represents one of amino acids or peptides consisting of 1 to 16 amino acid residues counted from the N-terminal side of Leu-Ala-Ala-Val-Leu-Gly-Lys-Arg-Tyr-Lys-Gln-Arg-Val-Lys-Asn-Lys (SEQ ID NO:21). In other words, Y represents Leu, Leu-Ala, Leu-Ala-Ala-Val (SEQ ID NO:22), Leu-Ala-Ala-Val-Leu (SEQ ID NO:23), Leu-Ala-Ala-Val-Leu-Gly (SEQ ID NO:24), Leu-Ala-Ala-Val-Leu-Gly-Lys (SEQ ID NO:25), Leu-Ala-Ala-Val-Leu-Gly-Lys-Arg (SEQ ID NO:26), Leu-Ala-Ala-Val-Leu-Gly-Lys-Arg-Tyr (SEQ ID NO:27), Leu-Ala-Ala-Val-Arg-Tyr-Lys (SEQ ID NO:14), Leu-Ala-Ala-Val-Leu-Gly-Lys-Arg-Tyr-Lys-Gln (SEQ ID NO:15), Leu-Ala-Ala-Val-Leu-Gly-Lys-Arg-Tyr-Lys-Gln-Arg (SEQ ID NO:16), Leu-Ala-Ala-Val-Leu-Gly-Lys-Arg-Tyr-Lys-Gln-Arg-Val (SEQ ID NO:17), Leu-Ala-Ala-Val-Leu-Gly-Lys-Arg-Tyr-Lys-Gln-Arg-Val-Lys (SEQ ID NO:18), Leu-Ala-Ala-Val-Leu-Gly-Lys-Arg-Tyr-Lys-Gln-Arg-Val-Lys-Asn (SEQ ID NO:19) or Leu-Ala-Ala-Val-Leu-Gly-Lys-Arg-Tyr-Lys-Gln-Arg-Val-Lys-Asn-Lys (SEQ ID NO:20).

In formula (I), the C-terminus is usually a carboxyl group (—COOH) or a carboxylate (—COO$^-$), but may be an amido group (—CONH$_2$) or an ester group (—COOR). Examples of R of the ester groups include lower alkyl groups such as $C_{1-6}$ alkyl groups (ex. methyl, ethyl, n-propyl, isopropyl or n-butyl); cycloalkyl groups such as $C_{3-8}$ cycloalkyl groups (ex. cyclopentyl or cyclohexyl); aryl groups such as $C_{6-12}$ aryl groups (ex. phenyl or α-naphthyl); aralkyl groups such as $C_{7-14}$ aralkyl groups (ex. phenyl-$C_{1-2}$alkyl such as benzyl, phenethyl or α-naphthyl-$C_{1-2}$alkyl such as α-naphthylmethyl). In addition, the ester groups also include pivaloyloxymethyl esters which are frequently used as oral esters. When the polypeptides represented by formula (I) have a carboxylic group(s) or carboxylate(s) at other than C-terminus, amide or ester derivatives at the above carboxylic or carboxylate group(s) are included in the polypeptides of the present invention. Examples of the esters include the above described esters at the C-terminus. In the present invention, it is preferred that the C-terminus is amide.

The pharmaceutically acceptable salts of the polypeptides represented by formula (I) (hereinafter referred to as polypeptides (I)) of the present invention include metal salts such as sodium salts, potassium salts, calcium salts, magnesium salts; inorganic acid addition salts such as hydrochlorides, sulfates and phosphates; and organic acid salts such as acetates, propionates, citrates, tartrates, malates and oxalates.

In this specification, amino acids and peptides are indicated by the abbreviations adopted by the IUPAC-IUB Commission on Biochemical Nomenclature or commonly used in the art. For example, the following abbreviations are used:

Gly: Glycine
Ala: Alanine
Val: Valine
Ile: Isoleucine
Leu: Leucine
Pro: Proline
Arg: Arginine
Lys: Lysine
His: Histidine
Asp: Aspartic acid
Asn: Asparagine
Glu: Glutamic acid
Gln: Glutamine
Ser: Serine
Thr: Threonine
Phe: Phenylalanine
Tyr: Tyrosine
Met: Methionine
Met(O): Methionine-S-oxide Protective groups and reagents commonly used in this specification are indicated by the following abbreviations:
Z: Benzyloxycarbonyl
Boc: t-Butoxycarbonyl
Bzl: Benzyl
Trt: Trityl
Bum: t-Butoxymethyl
Br-Z: 2-Bromobenzyloxycarbonyl
Cl-Z: 2-Chlorobenzyloxycarbonyl
Cl$_2$-Bzl: 2,6-Dichlorobenzyl
Tos: p-Toluenesulfonyl
Mts: 2,4,6-Trimethylbenzenesulfonyl
Bom: Benzyloxymethyl
Fmoc: 9-Fluorenylmethyloxycarbonyl
NO$_2$: Nitro
DNP: Dinitrophenyl
PAM: Phenylacetamidomethyl
DEAE: Diethylaminoethyl
OBzl: Benzyl ester
OcHex: Cyclohexyl ester
DCC: N,N'-Dicyclohexylcarbodiimide
HOBt: 1-Hydroxybenzotriazole
HOOBt: 3-Hydroxy-4-oxo-3,4-dihydrobenzotriazine
HONB: N-Hydroxy-5-norbornene-2,3-dicarboxyimide
DMF: N,N-Dimethylformamide
BRA: Benzhydrylamine The polypeptides (I) of the present invention can be produced by methods for peptide synthesis known in the art. Examples, of such methods for peptide synthesis include methods described in M. Bodansky and M. A. Ondetti, *Peptide Synthesis*, Interscience, New York (1966); F. M. Finn and K. Hofmann, *The Proteins*, Vol. 2, edited by H. Nenrath and R. L. Hill, Academic Press, New York, (1976); N. Izumiya et al., *Peptide Gosei no Kiso to Jikken* (*Fundamentals and Experiments of Peptide Synthesis*), Maruzen (1985); H. Yazima, S. Sakakibara et al., *Seikagaku Jikken Koza* (*Course of Biochemical Experiments*), 1, edited by Biochemical Society of Japan, Tokyo Kagaku Dojin (1977); H. Kimura et al., *Zoku Seikagaku Jikken Koza* (*Course of Biochemical Experiments, second series*), 2, edited by Biochemical Society of Japan, Tokyo Kagaku Dojin (1987); and J. M. Stewart and J. D. Young, *Solid Phase Peptide Synthesis*, Pierce Chemical Company, Illinois (1984), namely, azide methods, chloride methods, acid anhydride methods, mixed acid anhydride methods, DCC methods, active ester methods, methods using Woodward reagent K, carbonylimidazole methods, oxidation-reduction methods, DCC/HONB methods and methods using BOP reagents.

The synthesis of the polypeptides (I) of the present invention may be conducted by either solid phase synthesis methods or liquid phase synthesis methods. In the present invention, the solid phase synthesis methods are more preferred. In the solid phase synthesis methods, insoluble resins known in the art are used. Examples of such insoluble resins include chloromethyl resins, hydroxymethyl resins, benzhydrylamine resins, aminomethyl resins, 4-benzyloxybenzyl alcohol resins, 4-methylbenzhydrylamine resins, PAM resins, 4-hydroxymethylphenylacetamidomethyl resins, polyacrylamide resins, 4-(2',4'-dimethoxyphenylhydroxymethyl)phenoxy resins and 4-(2',4'-dimethoxyphenyl-Fmoc-aminoethyl)phenoxy resins.

Using these resins, protected amino acids are normally condensed in turn from the C-termini of polypeptides (I) according to the amino acid sequences thereof and all protective groups are eliminated by protective group eliminating treatment, whereby desired polypeptides (I) can be synthesized. Carboxylic group(s) or carboxylate(s) of the resulting polypeptides may be further subjected to amidation or esterification to synthesize other polypeptides of the present invention. Furthermore, one or more peptide fragments of the present polypeptides can be synthesized by the above described methods, and the fragments can be condensed with each other to obtain the polypeptides of the present invention.

With respect to the condensation of protected amino acids, various activating reagents available for peptide synthesis can be used, and particularly, carbodiimides are preferably used among others. The carbodiimides include DCC, N,N'-diisopropylcarbodiimide and N-ethyl-N'-(3-dimethylaminopropyl)carbodiimide. In activation with these reagents, the protected amino acids can be added to the resins together with racemization inhibiting additives (for example, HOBt and HOOBt), or can previously be activated as symmetrical acid anhydrides, HOBt esters or HOOBt esters, followed by addition to the resins. Solvents used for the activation of the protected amino acids or the condensation thereof with the resins can be appropriately selected from the solvents known to be commonly used in peptide condensation reactions. Examples of the solvents include DMF, dimethyl sulfoxide, pyridine, chloroform, dioxane, methylene chloride, tetrahydrofuran, acetonitrile, ethyl acetate, N-methylpyrrolidone and appropriate mixtures thereof.

The reaction temperature is appropriately selected from the temperature range commonly used in peptide bond-forming reactions, usually from the range of about −20° to about 30° C. The activated amino acid derivatives are usually used 1.5 to 4 times in excess. As a result of a test using the ninhydrin reaction, if the condensation is insufficient, the condensation reaction is repeated without elimination of the protective groups, whereby the condensation can be sufficiently conducted. If the condensation can not be sufficiently carried out even by repetition of the reaction, unreacted amino acids can be acetylated using acetic anhydride or acetylimidazole.

Examples of the protective groups for the amino group of raw materials include z, Boc, t-amyloxycarbonyl, isobornyloxycarbonyl, 4-methoxybenzyloxycarbonyl, Cl-Z, Br-Z, adamantyloxycarbonyl, trifluoroacetyl, phthalyl, formyl, 2-nitrophenylsulfenyl, diphenylphosphinothioyl and Fmoc. The protective groups for the carboxyl group include, for example, alkyl esters (such as esters of methyl, ethyl, propyl, butyl, t-butyl, cyclopentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, benzyloxycarbonylhydrazide, t-butyloxycarbonylhydrazide and tritylhydrazide.

The hydroxyl group of serine can be protected, for example, by esterification or etherification. Examples of groups suitable for this esterification include lower alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl.

Examples of the protective groups for the phenolic hydroxyl group of tyrosine include Bzl, $Cl_2$-Bzl, 2-nitrobenzyl, BrZ, and t-butyl. The protective groups for the imidazole ring of histidine include Tos, 4-methoxy-2,3,6-trimethylbenzenesulfonyl, DNP, benzyloxymethyl, Bum, Boc, Trt and Fmoc.

Examples of the reactive carboxyl groups of the raw materials include the corresponding acid anhydrides, azide and active esters (esters of alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt. Examples of the activated amino groups of the raw materials include the corresponding phosphoric acid amides.

Methods for eliminating the protective groups include, for example, catalytic reduction in a stream of hydrogen in the presence of a catalyst such as Pd black or Pd-carbon, acid treatment with anhydrous hydrogen fluoride, methanesulfonic acid, trifluoromethanesulfonic acid, trifluoroacetic acid or mixtures thereof, and reduction with sodium in liquid ammonia. The elimination reaction by the above-mentioned acid treatment is generally conducted at a temperature of about −20° to about 40° C. In the acid treatment, it is effective to add a cation trapping agent such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is eliminated by thiophenol treatment. The formyl group used as the protective group for the indole ring of tryptophan may be eliminated by either (i) alkali treatment using dilute sodium hydroxide, dilute ammonia or the like, or (ii) the above-mentioned elimination by the acid treatment in the presence of 1,2-ethanedithiol, 1,4-butanedithiol or the like.

The protection of functional groups not to be related to the reaction of the raw materials, the protective groups, the elimination of the protective groups and the activation of functional groups related to the reaction can also be appropriately selected from groups or methods known in the art.

After completion of the reaction, polypeptides (I) thus obtained are collected by conventional separation and purification methods of peptides such as extraction, distribution, reprecipitation, recrystallization, column chromatography and high performance liquid chromatography.

Since the present polypeptides (I) do not have Met residue in the molecule, they are stable to oxidation as a product or during the production procedure.

Polypeptides (I) of the present invention may also be obtained by methods known in the art as metal salts such as sodium salts, potassium salts, calcium salts and magnesium salts, as salts with bases or basic compounds such as ammonium salts and arginine salts, or as acid addition salts, particularly pharmaceutically acceptable acid addition salts. Examples thereof include salts of inorganic acids (such as hydrochloric acid, sulfuric acid and phosphoric acid) or organic acids (such as acetic acid, propionic acid, citric acid, tartaric acid, malic acid, oxalic acid and methanesulfonic acid).

Amidation or esterification of the carboxylic group(s) or carboxylate(s) of the polypeptide represented by formula (I) can be conducted by the known methods or the similar methods.

The c-AMP-producing activity was assayed using rat adrenal medulla-derived subcultured cells PC12h by measuring the amount of c-AMP secreted from the cells with a kit for assaying c-AMP. As a result, the activity equivalent to that of PACAP27 was observed in polypeptides (I) of the present invention, as shown in FIG. 1.

In order to clarify that the polypeptides of the present invention are not easily oxidized, oxidized product content (%) of $Arg^{17}$-PACAP27 obtained in Example 1 below were assayed when stored both in lyophylization and in aqueous acetic acid. The assay of the oxidized product content (%) were conducted on High Performance Liquid Chromatography (HPLC). The results are shown in Table 1.

Conditions of HPLC are as follows

Column: YMC ODS AM-301 (4.6×100 mm)
Eluents: Solution A 0.1% aqueous trifluoroacetic acid
Solution B acetonitrile containing 0.1% trifluoroacetic acid
A linear gradient elution from solution A to solution B for 50 minutes
Flow rate: 1.0 ml/min
Elution time of $Arg^{17}$-PACAP27: 19.9 min

TABLE 1

| Sample | Oxidized product (%) | | |
|---|---|---|---|
| | just after synthesizing | lyophilization store | aqueous acetic acid |
| $Arg^{17}$-PACAP27 obtained in Example 1 | 0 | 0 | 0 |

Table 1 shows that the polypeptides of the present invention are not easily oxidized.

Novel polypeptides (I) of the present invention (including the amides, esters and salts thereof) enhance the production of c-AMP. For this reason, novel polypeptides (I) of the present invention can be used, for example, as nerve activating agents such as an agent which can increase the survival time of nerve cells. Specifically, they can be used as therapeutic agents for various neuropathy or repairing agents for the damaged nerves in mammals such as sheep, rats and humans. Furthermore, novel polypeptides (I) of the present invention have gastric inhibitory activity.

Polypeptides (I) of the present invention, when used as the above-mentioned neuropathy therapeutic agents and damaged nerve repairing agents, can be safely administered orally or parenterally in the form of powders, granules, tablets, capsules, injections, suppositories, ointments or sustained release preparations, alone or in combination with pharmaceutically acceptable carriers, excipients or diluents. Polypeptides (I) of the present invention are typically administered parenterally, for example, by intravenous or subcutaneous injection, intraventricular or intraspinal administration, nasotracheal administration or intrarectal administration. In some cases, however, they are administered orally.

Polypeptides (I) of the present invention are stable substances, and therefore, can be stored as physiological saline solutions. It is also possible to lyophilize the polypeptides, store them in ampules with mannitol or sorbitol, and dissolve them in a suitable carrier at the time of use. Polypeptides (I) of the present invention can be given in their free forms, or in the form of alkali addition salts or acid addition salts thereof. All of the free peptides, the alkali addition salts and the acid addition salts thereof are generally given in a proper dose within the range of 0.1 nmole to 1 µmole of free peptide per kg of weight.

More specifically, the dosage varies depending on the type of disease to be treated, the symptom of the disease, the object to which the agents are given and the route of administration. For example, when given by injection to adult patients, it is advantageous that the active ingredients (polypeptides (I)) are normally given in one dose of about 0.1 nmole to 1 µmole/kg of weight, preferably 1 nmole to 0.1 µmole/kg of weight, about once to 3 times a day. Drip infusion is also effective. In this case, the total dosage is the same as with injection.

When these polypeptides are used as therapeutic agents, they are required to be carefully purified so as to contain no bacteria and no pyrogens. No toxicity is detected in the purified polypeptides of the present invention.

The present invention will be described in more detail with the following examples, reference example and experimental example. In the examples and reference example, all amino acid residues take the L-form.

EXAMPLE 1

Synthesis of $Arg^{17}$-PACAP27-$NH_2$ (H-His-Ser-Asp-Gly-Ile-Phe-Thr-Asp-Ser-Tyr-Ser-Arg-Tyr-Arg-Lys-Gln-Arg-Ala-Val-Lys-Lys-Tyr-Leu-Ala-Ala-Val-Leu-$NH_2$) [Ia] (SEQ ID NO: 2)

Synthesis was carried out using 0.60 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Arg(Tos), Boc-Gln, Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, unreacted amino acids were acetylated with acetic anhydride to obtain 1.34 g of a protected peptide resin.

0.89 g of the resulting protected peptide resin was treated with 10 ml of anhydrous hydrogen fluoride in the presence of 1.52 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and subjected to a LiChroprep RP-18 column (2.6×9.2 cm) again to conduct elution by a linear gradient of from 20% to 40% aqueous acetonitrile containing 0.1% trifluoroacetic acid. Then, the main fractions were collected and lyophilized. The resulting product was dissolved in 20 ml of a 0.05M solution of acetic acid in aqueous ammonia. The solution thus obtained was subjected to a CM-Cellulofine resin column (2.5×10 cm) and eluted by a linear gradient of from 0.05M to 0.5M ammonium acetate buffer solution. The main fractions were combined, followed by lyophilization. Thus, 9.6 mg of a white powder was obtained.

Anal. for amino acids

Asp 1.98(2), Thr 0.90(1), Ser 2.26(3), Glu 1.10(1), Gly 1.10(1), Ala 2.95(3), Val 1.93(2), Ile 0.97(1), Leu 2.00(2), Tyr 2.87(3), Phe 0.98(1), Lys 2.87(3), His 1.02(1), Arg 2.89(3)

$(M+H)^+$ by mass spectrography: 3171.8710

HPLC elution time: 20.3 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 2

Synthesis of $Ser^{17}$-PACAP27-$NH_2$ (H-His-Ser-Asp-Gly-Ile-Phe-Thr-Asp-Ser-Tyr-Ser-Arg-Tyr-Arg-Lys-Gln-Ser-Ala-Val-Lys-Lys-Tyr-Leu-Ala-Ala-Val-Leu-$NH_2$) [Ib] (SEQ ID NO: 3)

Synthesis was carried out using 0.74 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Ser(Bzl), Boc-Gln, Boc-Arg(Tos), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, unreacted amino acids were acetylated with acetic anhydride to obtain 2.82 g of a protected peptide resin.

1.01 g of the resulting protected peptide resin was treated with 10 ml of anhydrous hydrogen fluoride in the presence of 1.62 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and subjected to a LiChroprep RP-18 column (2.6×9.2 cm) again to conduct elution by a linear gradient of from 20% to 40% aqueous acetonitrile containing 0.1% trifluoroacetic acid. Then, the main fractions were collected and lyophilized. The resulting product was dissolved in 20 ml of a 0.05M solution of acetic acid in aqueous ammonia. The solution thus obtained was subjected to a CM-Cellulofine resin column (2.5×10 cm) and eluted by a linear gradient of from 0.05M to 0.5M ammonium acetate buffer solution. The main fractions were combined, followed by lyophilization. Thus, 17.7 mg of a white powder was obtained.

Anal. for amino acids

Asp 2.03(2), Thr 0.98(1), Ser 3.53(4), Glu 1.13(1), Gly 1.03(1), Ala 3.13(3), Val 1.93(2), Ile 0.90(1), Leu 2.00(2), Tyr 3.01(3), Phe 0.92(1), Lys 2.96(3), His 1.10(1), Arg 2.01(2)

$(M+H)^+$ by mass spectrography: 3102.7930

HPLC elution time: 21.0 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 3

Synthesis of $Phe^{17}$-PACAP27-$NH_2$ (H-His-Ser-Asp-Gly-Ile-Phe-Thr-Asp-Ser-Tyr-Ser-Arg-Tyr-Arg-Lys-Gln-Phe-Ala-Val-Lys-Lys-Tyr-Leu-Ala-Ala-Val-Leu-$NH_2$) [Ic] (SEQ ID NO: 4)

Synthesis was carried out using 0.72 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Phe, Boc-Gln, Boc-Arg(Tos), Boc-Ser(Bzl), Boc-Gly, Boc-Asp(OcHex), Boc-Thr(Bzl), Boc-Ile and Boc-His(Bom)

After the same amino acid derivatives activated with DCC or HOBt/DCC were further condensed again, unreacted amino acids were acetylated with acetic anhydride to obtain 2.96 g of a protected peptide resin.

0.98 g of the resulting protected peptide resin was treated with 10 ml of anhydrous hydrogen fluoride in the presence of 1.62 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and lyophilized. The resulting product was dissolved in 20 ml of a 0.05M ammonium acetate buffer solution. The solution thus obtained was subjected to a CM-Cellulofine resin column (2.5×10 cm) and eluted by a linear gradient of from 0.05M to 0.5M solutions of acetic acid in aqueous ammonia. The main fractions were combined and lyophilized to obtain 24 mg of a white powder.

Anal. for amino acids

Asp 1.98(2), Thr 0.90(1), Ser 2.26(3), Glu 1.10(1), Gly 1.02(1), Ala 3.10(3), Val 1.88(2), Ile 0.88(1), Leu 2.00(2), Tyr 3.09(3), Phe 1.90(2), Lys 2.90(3), His 1.00(1), Arg 1.99(2)

$(M+H)^+$ by mass spectrography: 3162.6340

HPLC elution time: 21.5 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 4

Synthesis of Leu$^{17}$-PACAP27-NH$_2$(H-His-Ser-Asp-Gly-Ile-Phe-Thr-Asp-Ser-Tyr-Ser-Arg-Tyr-Arg-Lys-Gln-Leu-Ala-Val-Lys-Lys-Tyr-Leu-Ala-Ala-Val-Leu-NH$_2$) [Id] (SEQ ID NO: 5)

Synthesis was carried out using 0.60 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Gln, Boc-Arg(Tos), Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, unreacted amino acids were acetylated with acetic anhydride to obtain 1.34 g of a protected peptide resin.

1.00 g of the resulting protected peptide resin was treated with 10 ml of anhydrous hydrogen fluoride in the presence of 1.61 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and lyophilized. The resulting product was dissolved in 20 ml of a 0.05M ammonium acetate buffer solution. The solution thus obtained was subjected to a CM-Cellulofine resin column (2.5×10 cm) and eluted by a linear gradient of from 0.05M to 0.5M solutions of acetic acid in aqueous ammonia. The main fractions were combined and lyophilized to obtain 35.4 mg of a white powder.

Anal. for amino acids

Asp 1.97(2), Thr 0.94(1), Ser 2.46(3), Glu 1.08(1), Gly 1.02(1), Ala 3.08(3), Val 1.93(2), Ile 0.94(1), Leu 3.00(3), Tyr 2.51(3), Phe 0.94(1), Lys 2.91(3), His 1.09(1), Arg 1.99(2)

$(M+H)^+$ by mass spectrography: 3128.5970

HPLC elution time: 21.5 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 5

Synthesis of Glu$^{17}$-PACAP27-NH$_2$ (H-His-Ser-Asp-Gly-Ile-Phe-Thr-Asp-Ser-Tyr-Ser-Arg-Tyr-Arg-Lys-Gln-Glu-Ala-Val-Lys-Lys-Tyr-Leu-Ala-Ala-Val-Leu-NH$_2$) [Ie] (SEQ ID NO: 6)

Synthesis was carried out using 0.74 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Arg(Tos), Boc-Gln, Boc-Ser(Bzl), Boc-Gly, Boc-Asp(OcHex), Boc-Thr(Bzl), Boc-Phe, Boc-Ile and Boc-His(Bom)

After the same amino acid derivatives activated with DCC or HOBt/DCC were further condensed again, unreacted amino acids were acetylated with acetic anhydride to obtain 1.94 g of a protected peptide resin.

0.93 g of the resulting protected peptide resin was treated with 10 ml of anhydrous hydrogen fluoride in the presence of 1.52 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and subjected to a LiChroprep RP-18 column (2.6×9.2 cm) again to conduct elution by a linear gradient of from 20% to 40% aqueous acetonitrile containing 0.1% trifluoroacetic acid. Then, the main fractions were collected and lyophilized. The resulting product was dissolved in 20 ml of a 0.05M ammonium acetate buffer solution. The solution thus obtained was subjected to a CM-Cellulofine resin column (2.5×10 cm) and eluted by a linear gradient of from 0.05M to 0.5M ammonium acetate buffer solution. The main fractions were combined, followed by lyophilization. Thus, 17.5 mg of a white powder was obtained.

Anal. for amino acids:

Asp 1.98(2), Thr 0.94(1), Ser 2.47(3), Glu 2.27(2), Gly 1.10(1), Ala 3.28(3), Val 1.92(2), Ile 0.93(1), Leu 2.00(2), Tyr 2.93(3), Phe 0.94(1), Lys 2.80(3), His 0.98(1), Arg 1.93(2)

$(M+H)^+$ by mass spectrography: 3144.6870

HPLC elution time: 21.2 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 6

Synthesis of $Gly^{17}$-PACAP27-$NH_2$ (H-His-Ser-Asp-Gly-Ile-Phe-Thr-Asp-Ser-Tyr-Ser-Arg-Tyr-Arg-Lys-Gln-Gly-Ala-Val-Lys-Lys-Tyr-Leu-Ala-Ala-Val-Leu-$NH_2$) [If] (SEQ ID NO: 7)

Synthesis was carried out using 0.64 g (0.5 mmole) of a commercial p-methyl BHA resin (Applied Biosystems Inc.) and a peptide synthesizer (Model 430A, Applied Biosystems Inc.).

A starting amino acid, Boc-Leu, was activated with HOBt/DCC and condensed to the resin. Thereafter, the Boc group on the resin was treated with 50% trifluoroacetic acid/methylene chloride to deprotect the amino group. The following protected amino acids were activated with HOBt/DCC, and then condensed to the free amino group in turn according to the above-mentioned amino acid sequence:

Boc-Val, Boc-Ala, Boc-Leu, Boc-Tyr(Br-Z), Boc-Lys(Cl-Z), Boc-Gly, Boc-Gln, Boc-Arg(Tos), Boc-Ser(Bzl), Boc-Asp(OcHex), Boc-Thr(Bzl), Boc-Phe, Boc-Ile and Boc-His(Bom)

After the same amino acid derivatives activated with DCC or HOBt/DCC were further condensed again, unreacted amino acids were acetylated with acetic anhydride to obtain 2.75 g of a protected peptide resin.

1.01 g of the resulting protected peptide resin was treated with 10 ml of anhydrous hydrogen fluoride in the presence of 1.63 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex G-25 column (2×75 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a LiChroprep RP-18 resin column (2.6×9.2 cm) and eluted by a linear gradient of 0.1% aqueous trifluoroacetic acid and 50% acetonitrile containing 0.1% trifluoroacetic acid. The main fractions were combined and subjected to a LiChroprep RP-18 column (2.6×9.2 cm) again to conduct elution by a linear gradient of from 20% to 40% aqueous acetonitrile containing 0.1% trifluoroacetic acid. Then, the main fractions were collected and lyophilized. The resulting product was dissolved in 20 ml of a 0.05M ammonium acetate buffer solution. The solution thus obtained was subjected to a CM-Cellulofine resin column (2.5×10 cm) and eluted by a linear gradient of from 0.05M to 0.5M ammonium acetate buffer solution. The main fractions were combined, followed by lyophilization. Thus, 20.5 mg of a white powder was obtained.

Anal. for amino acids

Asp 1.97(2), Thr 0.93(1), Ser 2.44(3), Glu 1.07(1), Gly 1.97(2), Ala 3.10(3), Val 1.93(2), Ile 0.94(1), Leu 2.00(2), Tyr 3.02(3), Phe 0.96(1), Lys 2.92(3), His 1.03(1), Arg 1.96(2)

$(M+H)^+$ by mass spectrography: 3072.6120

HPLC elution time: 20.7 minutes

Column conditions

Column: Wakosil 5C18 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

EXAMPLE 7

Synthesis of $Arg^{17}$-PACAP26-$NH_2$ (H-His-Ser-Asp-Gly-Ile-Phe-Thr-Asp-Ser-Tyr-Ser-Arg-Tyr-Arg-Lys-Gln-Arg-Ala-Val-Lys-Lys-Tyr-Leu-Ala-Ala-Val-$NH_2$) [Ih] (SEQ ID NO: 8)

The above-mentioned polypeptide [Ih] was synthesized in accordance with the method of Example 1 using a p-methyl BHA resin and a peptide synthesizer. As a starting amino acid, Boc-Val was used in lieu of Boc-Leu.

EXAMPLE 8

Synthesis of $Arg^{17}$-PACAP23-$NH_2$(H-His-Ser-Asp-Gly-Ile-Phe-Thr-Asp-Ser-Tyr-Ser-Arg-Tyr-Arg-Lys-Gln-Arg-Ala-Val-Lys-Lys-Tyr-Leu-$NH_2$) [Ii] (SEQ ID NO: 9)

The above-mentioned polypeptide [Ii] was synthesized in accordance with the method of Example 1 using a p-methyl BHA resin and a peptide synthesizer.

EXAMPLE 9

Synthesis of $Arg^{17}$-PACAP38-$NH_2$ (H-His-Ser-Asp-Gly-Ile-Phe-Thr-Asp-Ser-Tyr-Ser-Arg-Tyr-Arg-Lys-Gln-Arg- Ala-Val-Lys-Lys-Tyr-Leu-Ala-Ala-Val-Leu-Gly-Lys-Arg-Tyr-Lys-Gln-Arg-Val-Lys-Asn-Lys-NH$_2$) [Ij] (SEQ ID NO: 10)

The above-mentioned polypeptide [Ij] was synthesized in accordance with the method of Example 1 using a p-methyl BHA resin and a peptide synthesizer as described below.

A starting amino acid, Boc-Lys(Cl-Z), was activated with an activating reagent and condensed to the resin. Thereafter, the Boc group on the resin was eliminated to deprotect the amino group. The following protected amino acids were condensed to the free amino group in turn according to the above-mentioned amino acid sequence with activating with an activating reagent:

Boc-Asn, Boc-Lys(Cl-Z), Boc-Val, Boc-Arg(Tos), Boc-Gln, Boc-Tyr(Br-Z), Boc-Gly, Boc-Leu, Boc-Ala, Boc-Ser(Bzl), Boc-Asp(OcHex), Boc-Thr(Bzl), Boc-Phe, Boc-Ile and Boc-His(Bom)

The resulting protected peptide resin was treated with hydrogen fluoride, and thereafter the residue was extracted with a solvent. The extract was subjected to a resin column to repeat separation and purification procedures. The main fractions were collected and lyophilized to obtain the desired product [Ij].

EXAMPLE 10

Synthesis of Ser$^{17}$-PACAP38-NH$_2$ (H-His-Ser-Asp-Gly-Ile-Phe-Thr-Asp-Ser-Tyr-Ser-Arg-Tyr-Arg-Lys-Gln-Ser-Ala-Val-Lys-Lys-Tyr-Leu-Ala-Ala-Val-Leu-Gly-Lys-Arg-Tyr-Lys-Gln-Arg-Val-Lys-Asn-Lys-NH$_2$) [Ik] (SEQ ID NO: 11)

The above-mentioned polypeptide [Ik] was synthesized in accordance with the method of Example 9 using a commercial p-methyl BHA resin and a peptide synthesizer.

EXAMPLE 11

Synthesis of Arg$^7$-PACAP27-OH (H-His-Ser-Asp-Gly-Ile-Phe-Thr-Asp-Ser-Tyr-Ser-Arg-Tyr-Arg-Lys-Gln-Arg-Ala-Val-Lys-Lys-Tyr-Leu-Ala-Ala-Val-Leu-OH [Il] (SEQ ID NO: 12)

Using a commercial Boc-Leu-OCH$_2$-PAM resin, the Boc group on the resin was treated with 50% trifluoroacetic acid/methylene chloride. Thereafter, the above-mentioned polypeptide [Il] was synthesized in accordance with the method of Example 1, condensing the amino acids in turn according to the above-mentioned amino acid sequence.

Reference Example

Synthesis of Met(O)$^{17}$-PACAP27-NH$_2$ (H-His-Ser-Asp-Gly-Ile-Phe-Thr-Asp-Ser-Tyr-Ser-Arg-Tyr-Arg-Lys-Gln-Met(O)-Ala-Val-Lys-Lys-Tyr-Leu-Ala-Ala-Val-Leu-NH$_2$)

PACAP27-NH$_2$ (10.15 mg) was dissolved in 1N acetic acid (1 ml), and 30% aqueous hydrogen peroxide (0.1 ml) was added thereto under ice cooling, followed by stirring for 10 minutes. Thereafter, 2.3 ml of a 20% aqueous solution of ascorbic acid was added thereto. The resulting solution was subjected to a Sephadex G-25 column (2×85 cm) charged with 1N acetic acid, and developed with the same solvent. Fractions of 102 to 156 ml were collected, followed by lyophilization. Thus, a white powder (9.25 mg) was obtained.

Asp 2.00(2), Thr 0.93(1), Ser 2.46(3), Glu 1.09(1), Gly 1.01(1), Ala 3.11(3), Val 1.91(2), Ile 1.06(1), Leu 1.99(2), Tyr 2.36(3), Phe 1.03(1), Lys 2.90(3), His 0.83(1), Arg 1.96(2)

(M+H)$^+$ by mass spectrography: 3163.6

HPLC elution time: 20.4 minutes

Column conditions

Column: YMC ODS AM 301 (4.6×100 cm)

Eluents: Solution A (0.1% aqueous trifluoroacetic acid)

Solution B (acetonitrile containing 0.1% trifluoroacetic acid)

A linear gradient elution from solution A to solution B for 50 minutes

Flow rate: 1.0 ml/minute

Experimental Example

Established cells derived from adrenal medullas, PC12h, were cultivated in Dulbecco's modified Eagle's medium containing 10% semi-fetal calf serum at 37° C. A 48-well collagen-treated plate was inoculated with 5×10$^4$ cells per well, and cultivation was conducted for 7 to 10 days. Then, the culture medium was changed to 500 μl of Hank's balanced salt solution, followed by standing at 37° C. for 30 minutes. A sample to be tested (each of the example compounds [Ia] to [If], PACAP38-NH$_2$ or PACAP27-NH$_2$) dissolved in the same solution was added thereto, and cultivation was conducted at 37° C. for 2 hours. Subsequently, the amount of c-AMP in this culture solution was assayed using a kit for measuring c-AMP (Amersham Inc.). Results thereof are shown in FIG. 1.

---

What is claimed is:

1. A method for increasing the survival time of nerve cells in a warm-blooded animal, which comprises administering to the warm-blooded animal an effective amount of a polypeptide represented by the following formula:

His-Ser-Asp-Gly-Ile-Phe-Thr-Asp-Ser-Tyr-Ser-Arg-Tyr-Arg-Lys-Gln-NH-CHX-CO-Ala-Val-Lys-Lys-Tyr-Y    (SEQ ID NO: 13)

wherein: NH-CHX-CO is Glu, Gly, Ser or Arg residue; and

Y is an amino acid residue Leu or a peptide selected from the group consisting of Leu-Ala, Leu-Ala-Ala, Leu-Ala-Ala-Val (SEQ ID NO: 22), Leu-Ala-Ala-Val-Leu (SEQ ID NO: 23), Leu-Ala-Ala-Val-Leu-Gly (SEQ ID NO:24), Leu-Ala-Ala-Val-Leu-Gly-Lys (SEQ ID NO:25), Leu-Ala-Ala-Val-Leu-Gly-Lys-Arg (SEQ ID NO: 26), Leu-Ala-Ala-Val-Leu-Gly-Lys-Arg-Tyr (SEQ ID NO: 27), Leu-Ala-Ala-Val-Leu-Gly-Lys-Arg-Tyr-Lys (SEQ ID NO: 14), Leu-Ala-Ala-Val-Leu-Gly-Lys-Arg-Tyr-Lys-Gln (SEQ ID NO: 15), Leu-Ala-Ala-Val-Leu-Gly-Lys-Arg-Tyr-Lys-Gln-Arg (SEQ ID NO: 16), Leu-Ala-Ala-Val-Leu-Gly-Lys-Arg-Tyr-Lys-Gln-Arg-Val (SEQ ID NO: 17), Leu-Ala-Ala-Val-Leu-Gly-Lys-Arg-Tyr-Lys-Gln-Arg-Val-Lys (SEQ ID NO: 18), Leu-Ala-Ala-Val-Leu-Gly-Lys-Arg-Tyr-Lys-Gln-Arg-Val-Lys-Asn (SEQ ID NO: 19) and Leu-Ala-Ala-Val-Leu-Gly-Lys-Arg-Tyr-Lys-Gln-Arg-Val-Lys-Asn-Lys (SEQ ID NO: 20), or a pharmaceutically acceptable amide, ester or salt thereof.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 38 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
His  Ser  Asp  Gly  Ile  Phe  Thr  Asp  Ser  Tyr  Ser  Arg  Tyr  Arg  Lys  Gln
 1                 5                        10                       15
Met  Ala  Val  Lys  Lys  Tyr  Leu  Ala  Ala  Val  Leu  Gly  Lys  Arg  Tyr  Lys
                   20                        25                       30
```

```
Gln Arg Val Lys Asn Lys
         35
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
His Ser Asp Gly Ile Phe Thr Asp Ser Tyr Ser Arg Tyr Arg Lys Gln
 1               5                  10                  15
Arg Ala Val Lys Lys Tyr Leu Ala Ala Val Leu
             20                  25
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
His Ser Asp Gly Ile Phe Thr Asp Ser Tyr Ser Arg Tyr Arg Lys Gln
 1               5                  10                  15
Ser Ala Val Lys Lys Tyr Leu Ala Ala Val Leu
             20                  25
```

( 2 ) INFORMATION FOR SEQ ID NO:4:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
His Ser Asp Gly Ile Phe Thr Asp Ser Tyr Ser Arg Tyr Arg Lys Gln
 1               5                  10                  15
Phe Ala Val Lys Lys Tyr Leu Ala Ala Val Leu
             20                  25
```

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
His Ser Asp Gly Ile Phe Thr Asp Ser Tyr Ser Arg Tyr Arg Lys Gln
 1               5                  10                  15
Leu Ala Val Lys Lys Tyr Leu Ala Ala Val Leu
             20                  25
```

( 2 ) INFORMATION FOR SEQ ID NO:6:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
His Ser Asp Gly Ile Phe Thr Asp Ser Tyr Ser Arg Tyr Arg Lys Gln
 1               5                  10                  15
Glu Ala Val Lys Lys Tyr Leu Ala Ala Val Leu
            20                  25
```

( 2 ) INFORMATION FOR SEQ ID NO:7:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
His Ser Asp Gly Ile Phe Thr Asp Ser Tyr Ser Arg Tyr Arg Lys Gln
 1               5                  10                  15
Gly Ala Val Lys Lys Tyr Leu Ala Ala Val Leu
            20                  25
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
His Ser Asp Gly Ile Phe Thr Asp Ser Tyr Ser Arg Tyr Arg Lys Gln
 1               5                  10                  15
Arg Ala Val Lys Lys Tyr Leu Ala Ala Val
            20                  25
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
His Ser Asp Gly Ile Phe Thr Asp Ser Tyr Ser Arg Tyr Arg Lys Gln
 1               5                  10                  15
Arg Ala Val Lys Lys Tyr Leu
            20
```

( 2 ) INFORMATION FOR SEQ ID NO:10:

( i ) SEQUENCE CHARACTERISTICS:

(A) LENGTH: 38 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

| His | Ser | Asp | Gly | Ile | Phe | Thr | Asp | Ser | Tyr | Ser | Arg | Tyr | Arg | Lys | Gln |
| 1 | | | | 5 | | | | | 10 | | | | | 15 | |

| Arg | Ala | Val | Lys | Lys | Tyr | Leu | Ala | Ala | Val | Leu | Gly | Lys | Arg | Tyr | Lys |
| | | | 20 | | | | | 25 | | | | | 30 | | |

| Gln | Arg | Val | Lys | Asn | Lys |
| | | | 35 | | |

(2) INFORMATION FOR SEQ ID NO:11:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:11:

| His | Ser | Asp | Gly | Ile | Phe | Thr | Asp | Ser | Tyr | Ser | Arg | Tyr | Arg | Lys | Gln |
| 1 | | | | 5 | | | | | 10 | | | | | 15 | |

| Ser | Ala | Val | Lys | Lys | Tyr | Leu | Ala | Ala | Val | Leu | Gly | Lys | Arg | Tyr | Lys |
| | | | 20 | | | | | 25 | | | | | 30 | | |

| Gln | Arg | Val | Lys | Asn | Lys |
| | | | 35 | | |

(2) INFORMATION FOR SEQ ID NO:12:

(i) SEQUENCE CHARACTERISTICS:
(A) LENGTH: 27 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:12:

| His | Ser | Asp | Gly | Ile | Phe | Thr | Asp | Ser | Tyr | Ser | Arg | Tyr | Arg | Lys | Gln |
| 1 | | | | 5 | | | | | 10 | | | | | 15 | |

| Arg | Ala | Val | Lys | Lys | Tyr | Leu | Ala | Ala | Val | Leu |
| | | | 20 | | | | | 25 | | |

(2) INFORMATION FOR SEQ ID NO:13:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:13:

| His | Ser | Asp | Gly | Ile | Phe | Thr | Asp | Ser | Tyr | Ser | Arg | Tyr | Arg | Lys | Gln |
| 1 | | | | 5 | | | | | 10 | | | | | 15 | |

| Xaa | Ala | Val | Lys | Lys | Tyr |
| | | | 20 | | |

(2) INFORMATION FOR SEQ ID NO:14:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:14:

Leu Ala Ala Val Leu Gly Lys Arg Tyr Lys
1               5                   10

( 2 ) INFORMATION FOR SEQ ID NO:15:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:15:

Leu Ala Ala Val Leu Gly Lys Arg Tyr Lys Gln
1               5                   10

( 2 ) INFORMATION FOR SEQ ID NO:16:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:16:

Leu Ala Ala Val Leu Gly Lys Arg Tyr Lys Gln Arg
1               5                   10

( 2 ) INFORMATION FOR SEQ ID NO:17:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:17:

Leu Ala Ala Val Leu Gly Lys Arg Tyr Lys Gln Arg Val
1               5                   10

( 2 ) INFORMATION FOR SEQ ID NO:18:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:18:

Leu Ala Ala Val Leu Gly Lys Arg Tyr Lys Gln Arg Val Lys
1               5                   10

( 2 ) INFORMATION FOR SEQ ID NO:19:

( i ) SEQUENCE CHARACTERISTICS:
   ( A ) LENGTH: 15 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:19:

Leu Ala Ala Val Leu Gly Lys Arg Tyr Lys Gln Arg Val Lys Asn
1               5                   10                  15

( 2 ) INFORMATION FOR SEQ ID NO:20:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:20:

Leu Ala Ala Val Leu Gly Lys Arg Tyr Lys Gln Arg Val Lys Asn Lys
1               5                   10                  15

( 2 ) INFORMATION FOR SEQ ID NO:21:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:21:

Leu Ala Ala Val Leu Gly Lys Arg Tyr Lys Gln Arg Val Lys Ala Lys
1               5                   10                  15

( 2 ) INFORMATION FOR SEQ ID NO:22:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:22:

Leu Ala Ala Val
1

( 2 ) INFORMATION FOR SEQ ID NO:23:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:23:

Leu Ala Ala Val Leu
1               5

( 2 ) INFORMATION FOR SEQ ID NO:24:

( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:24:

Leu Ala Ala Val Leu Gly
1                     5

( 2 ) INFORMATION FOR SEQ ID NO:25:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:25:

Leu Ala Ala Val Leu Gly Lys
1                     5

( 2 ) INFORMATION FOR SEQ ID NO:26:

( i ) SEQUENCE CHARACTERISTICS:
            ( A ) LENGTH: 8 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:26:

Leu Ala Ala Val Leu Gly Lys Arg
1                     5

( 2 ) INFORMATION FOR SEQ ID NO:27:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:27:

Leu Ala Ala Val Leu Gly Lys Arg Tyr
1                     5